United States Patent
Gunduz et al.

(10) Patent No.: US 12,048,781 B2
(45) Date of Patent: Jul. 30, 2024

(54) BIOMIMETIC ARTIFICIAL BLOOD VESSEL AND A PRODUCTION METHOD THEREOF

(71) Applicants: T.C ISTANBUL MEDIPOL ÜNIVERSITESI, Istanbul (TR); T.C. MARMARA UNIVERSITESI, Istanbul (TR)

(72) Inventors: Oguzhan Gunduz, Tuzla (TR); Ahmet Zeki Sengil, Istanbul (TR); Faik Nuzhet Oktar, Istanbul (TR); Nazmi Ekren, Istanbul (TR); Selami Cakmak, Istanbul (TR); Ahmet Talat Inan, Istanbul (TR); Mehmet Onur Aydogdu, Istanbul (TR); Esra Altun, Istanbul (TR)

( * ) Notice: Subject to any disclaimer, the term of this patent is extended or adjusted under 35 U.S.C. 154(b) by 1291 days.

(21) Appl. No.: 16/612,677

(22) PCT Filed: May 16, 2018

(86) PCT No.: PCT/TR2018/050240
§ 371 (c)(1),
(2) Date: Nov. 11, 2019

(87) PCT Pub. No.: WO2019/032069
PCT Pub. Date: Feb. 14, 2019

(65) Prior Publication Data
US 2020/0061247 A1   Feb. 27, 2020

(30) Foreign Application Priority Data
May 16, 2017   (TR) .................................. 2017/07216

(51) Int. Cl.
A61L 27/50    (2006.01)
A61F 2/06     (2013.01)
A61L 27/20    (2006.01)
A61L 27/24    (2006.01)
A61L 27/26    (2006.01)
(Continued)

(52) U.S. Cl.
CPC .............. *A61L 27/507* (2013.01); *A61F 2/06* (2013.01); *A61L 27/20* (2013.01); *A61L 27/24* (2013.01); *A61L 27/26* (2013.01); *D01D 1/02* (2013.01); *D01D 5/003* (2013.01); *D01F 2/24* (2013.01); *A61L 27/18* (2013.01); *D10B 2509/00* (2013.01)

(58) Field of Classification Search
CPC .......... A61F 2/06; A61L 27/507; D01D 5/003
See application file for complete search history.

(56) References Cited

U.S. PATENT DOCUMENTS

2006/0204539 A1   9/2006   Atala et al.
2015/0273119 A1   10/2015  Heo et al.

FOREIGN PATENT DOCUMENTS

CN   101385872 A   3/2009
CN   104562438 A   4/2015
(Continued)

OTHER PUBLICATIONS

International Search Report for corresponding PCT/TR2018/050240.
Written Opinion of the ISA for corresponding PCT/TR2018/050240.

*Primary Examiner* — William H Matthews
(74) *Attorney, Agent, or Firm* — Egbert, McDaniel & Swartz, PLLC

(57) ABSTRACT

A three-dimensional biomimetic artificial blood vessel that is biodegradable and biocompatible, is inspired by the morphological structure and physiological role of blood (Continued)

Figure 1:
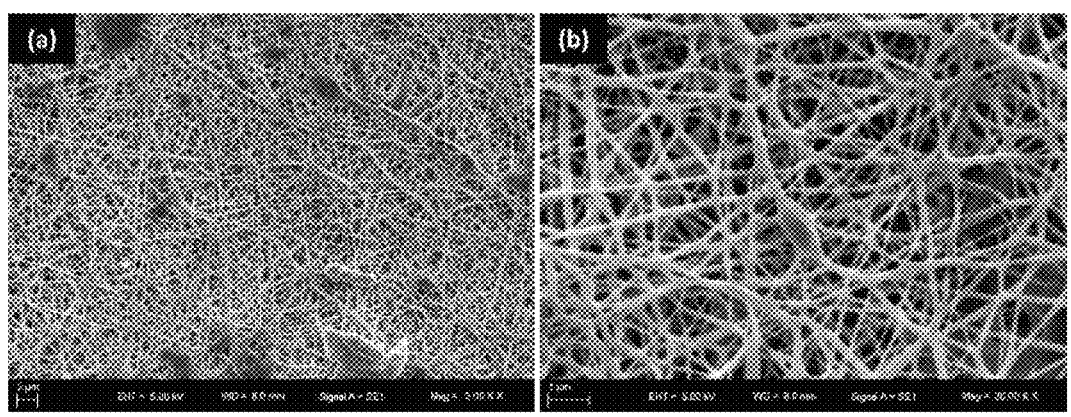

vessels having small diameter in the human circulatory system. A method of production by electro spinning is also disclosed.

20 Claims, 3 Drawing Sheets

(51) Int. Cl.
*D01D 1/02* (2006.01)
*D01D 5/00* (2006.01)
*D01F 2/24* (2006.01)
*A61L 27/18* (2006.01)

(56) References Cited

FOREIGN PATENT DOCUMENTS

| CN | 105079874 A | 11/2015 |
| WO | 2013109642 A1 | 7/2013 |
| WO | 2016138701 A1 | 9/2016 |

BIOMIMETIC ARTIFICIAL BLOOD VESSEL AND A PRODUCTION METHOD THEREOF

TECHNICAL FIELD

This invention relates to a three-dimensional biomimetic artificial blood vessel that is biodegradable and biocompatible, inspired by the morphological structure and physiological role of blood vessels having small diameter in the human circulatory system, and the method of production by means of electrospinning.

PRIOR ART

Cardiovascular system diseases are one of the leading health problems when examined in terms of mortality and morbidity rates worldwide. Studies in the field of tissue engineering in order to prevent or cure these kind of diseases have been promising.

The blood vessels, which are important components of the circulatory system, can lose their function due to congestion or different health problems and can lead to major health problems by causing blood flow continuity interruption to the region. Although these modern therapies, which are often used today, based on the ability to remove intraventricular obstruction by mechanical means are life-saving, there is the possibility of restenosis, vessel narrowing or collapse and similar complications that occur after treatment. At the same time, due to high treatment costs, it creates an economic burden in the countries that allocate a share of treatment for circulatory system diseases for both individuals and health insurances.

One of the most frequently methods used today comprise transfer of blood vessels having small diameters in an allogenic or autologous way. However, the difficulty of finding suitable donors and the possible rejection of tissue from the immune system limit the clinical practice of such treatments. For these reasons, production of blood vessels having a small diameter having mechanical properties suitable for their purpose of use with biocompatible materials hold a great deal of promise by means of modernizing present treatment methods and value added to patient's life. However, it is known that the materials produced for this purpose and the work done in this area have disadvantages of lacking essential features and requirements sought in an artificial blood vessel such as lack of biocompatibility, not preventing clotting, not having appropriate mechanical properties, not being suitable for long-term use.

In the known state of the art, WO2013109642 discloses compositions comprising a nanofiber framework having a printed configuration that mimics a tissue structure such as heart tissue, which is fertilized with one or more related stem cells. The invention described in said document further discloses, methods for treating damaged heart tissue in a damaged heart by providing application of the composition in an effective amount to the damaged cardiac tissue. This document also describes methods for preparing nanofiber tissue scaffold compositions. Said tissue scaffold is obtained by electrospinning using biocompatible polycaprolactone polymer and also by attaching an extracellular matrix protein onto the nanofiber scaffold. In the said invention, collagen is used as extracellular matrix protein.

In United States patent no. US2006204539, which is part of the state of the art, refers to compositions and methods for preparing electrospun matrices containing at least one natural biological material and at least one synthetic polymer material. The invention described in the document discloses that while the natural component matrices are highly biocompatible, the polymer component imparts an additional mechanical strength to the molecular weight scaffold and/or facilitates production by increasing the viscosity and bending properties of the solution during electrospinning. The object of the present invention is to obtain electrospun matrices for use in blood vessels, heart valves, vascular or cardiac structures. It is mentioned in said document that the electrospun nanofibers comprise polycaprolactone, collagen or cellulose derivatives.

BRIEF DESCRIPTION OF THE INVENTION

The object of this invention is to realize an artificial blood vessel which is suitable for use in the human body and which does not cause intra-arterial clotting, is composed of nano-sized fiber scaffold with high mechanical properties and elasticity against blood pressure, other external factors and aging effects and a production method thereof.

Another object of the invention is to realize an artificial blood vessel having endothelization stimulating and supporting effect on the outer wall and production thereof with electrospinning technique.

Another object of the invention is to realize an artificial blood vessel having a nanocomposite structure skeleton formed by superimposed nano-sized fibers made of natural and synthetic polymers and a method for production thereof.

DETAILED DESCRIPTION OF THE INVENTION

A "Biomimetic Artificial Blood Vessel and Production Method Thereof" to achieve the purpose of this invention is illustrated in the attached figures, wherein said figures disclose;

FIG. 1: The SEM (Scanning Electron Microscope) image of the artificial blood vessel scaffold of the present invention.

Figure 2:
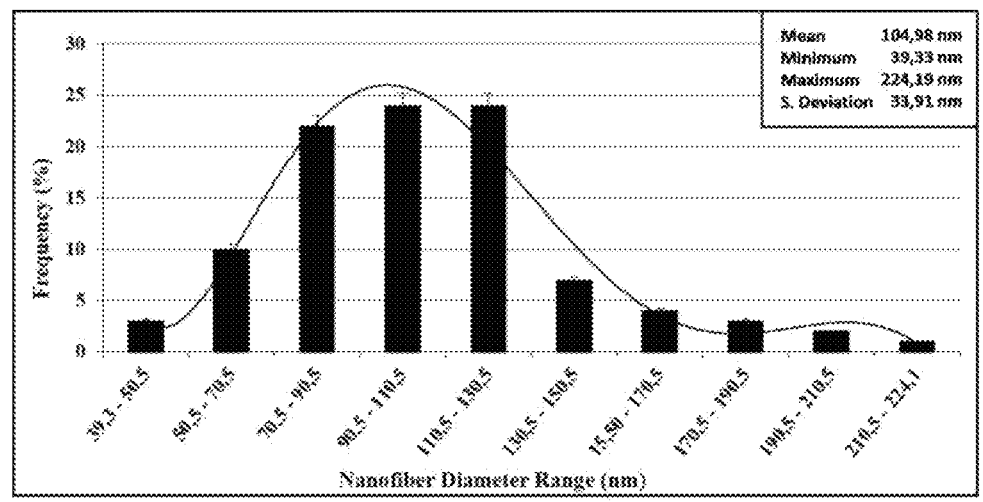

(a) Image of an artificial blood vessel structure scaffold of the invention at magnification of 5.00 KX (b) Image of an artificial blood vessel structure scaffold of the invention at magnification of 20.00 KX FIG. 2: Fiber dimensions frequency graph of the artificial blood vessel scaffold of the present invention.

Figure 3:
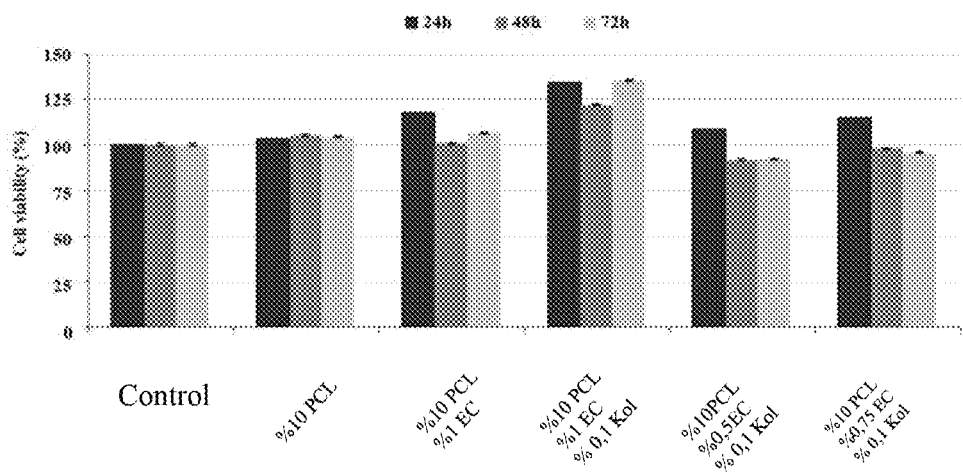

FIG. 3: The column charts showing the in-vitro cytotoxicity results measured for 24, 48 and 72 hours, respectively, according to the changing contents of biomimetic artificial veins.

Figure 4:
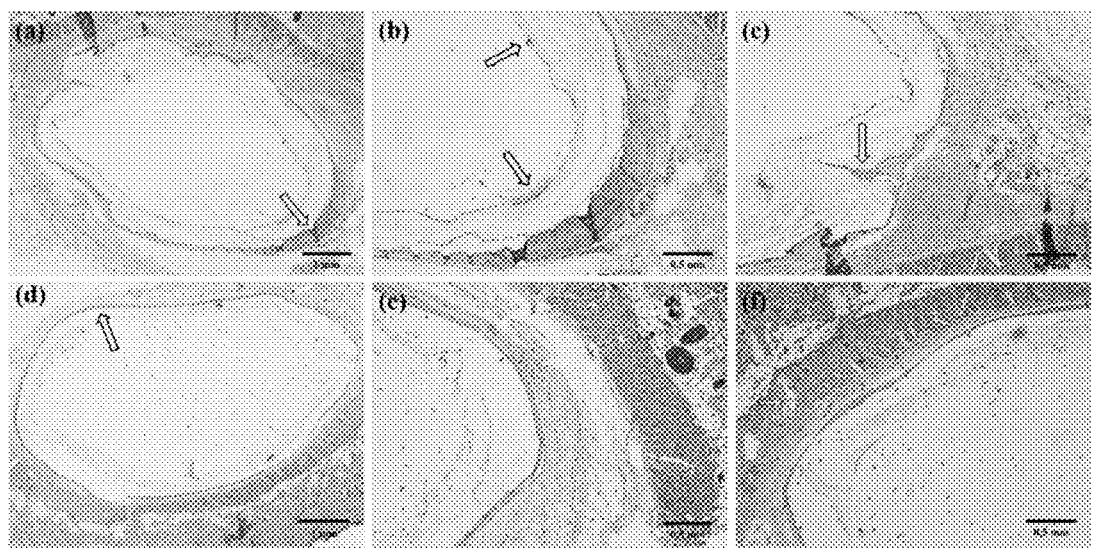

FIG. 4: Comparative analysis photos of tissue response after pathological examinations performed after 6 weeks of in-vitro testing.

In collagen-free specimens;

(a) At 20× magnification, the arrow indicates the thickest zone of inflammation.

(b) At 40× magnification, upper arrow points to the giant cell and lower arrow points to plasma and lymphocyte cells that entered the lumen.

(c) At 40× magnification, the arrow indicates proliferation of connective tissue.

In collagen containing specimens;

(d) At 20× magnification, the arrow indicates the thickest zone of inflammation.

(e and f) are photos taken at 40× magnification.

Figure 5:
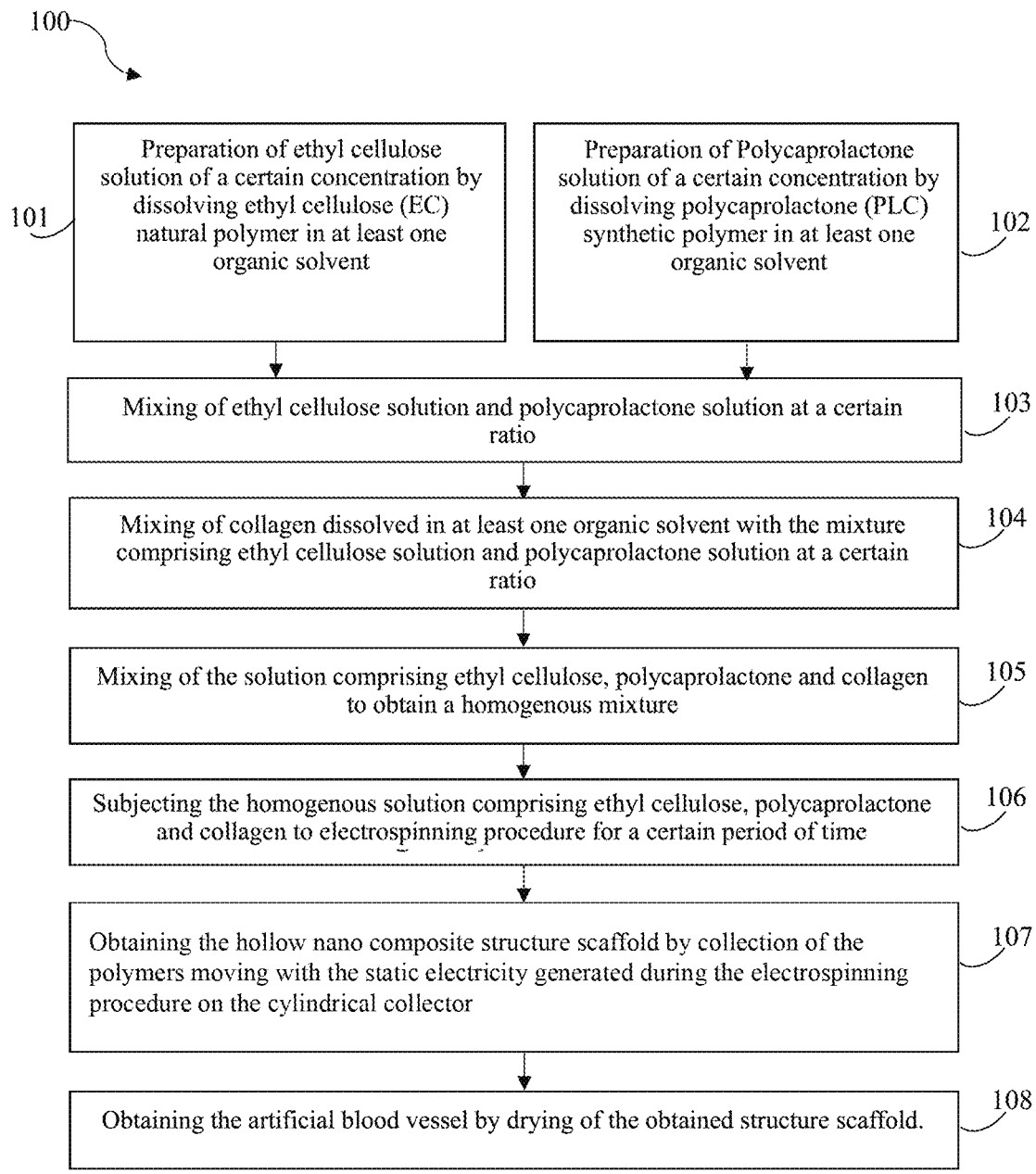

FIG. 5: The flow diagram of the production method for artificial blood vessel according to the invention.

The artificial blood vessel of the invention is suitable for use in the human body, it does not cause intra-arterial clotting and made up of nano composite structure scaffolds that has strong mechanical properties against blood pressure, outer effects and ageing and has strong elasticity. The artificial blood vessels of the invention are made up of the abovementioned nanocomposite structure and they have endothelization stimulating and supporting effect and they are biocompatible and biodegradable.

To this end, the artificial blood vessel forming structure scaffold of the invention comprises Polycaprolactone (PCL), that is a synthetic polymer and which has strong mechanical properties and is suitable for use in electrospinning technique; Ethyl cellulose (EC), that is a natural polymer and which is biocompatible and has low toxicity; and Collagen, which is one of the building blocks of the extracellular matrix and thus imitating it and also provides cell accumulation of the structure scaffolds. The collagen structure also provides elasticity to the structure scaffold and contributes to biocompatibility and endothelization.

According to present invention, a method for production of biomimetic artificial blood vessel (100) comprises the steps of Preparation of ethyl cellulose solution (101) at a certain concentration by dissolving biocompatible and low toxicity natural ethyl cellulose polymer in at least one organic solvent, Preparation of polycaprolactone solution (102) at a certain concentration by dissolving the synthetic polycaprolactone polymer in at least one organic solvent, Mixing the ethylcellulose solution and the polycaprolactone solution at a certain ratio (103)

Addition of collagen dissolved in at least one organic solvent into the mixture comprising ethyl cellulose and polycaprolactone solution (104), at a certain ratio Stirring the mixture comprising ethyl cellulose, polycaprolactone and collagen to have a homogenous solution (105), Subjecting the homogenous solution comprising ethyl cellulose, polycaprolactone and collagen to the electrospinning process (106) for a while in an electrospinning machine that comprise at least one needle and a movable, cylindrical collector via adjusting parameters of voltage, distance between the needle and the collector and flow rate that effect the nanofiber diameter and morphology, Obtaining the hollow nano-composite structure scaffold (107) via subjecting the mixture to electrospinning (106) and then collecting the nanofibers formed by movement of the polymers with the static electricity to form nanofibers on the cylindrical collector, Obtaining of the artificial blood vessel (108) via drying of the obtained structure scaffold.

In a preferred embodiment of the method for artificial blood vessel production (100) according to invention, the ethyl cellulose is dissolved in the organic solvent such that there is 1% of ethyl cellulose in the solution by weight. In order to obtain this, the ethyl cellulose solution (101) is prepared by addition of ethyl cellulose to a solution comprising dimethylacetamide (DMA) and tetrahydrofuran (THF) in a ratio of 60:40 by weight.

In a preferred embodiment of the artificial blood vessel manufacturing method (100) of the invention, the polycaprolactone solution (102) is prepared by adding polycaprolactone polymer to the solvent preferably comprising dimethylacetamide (DMA) and tetrahydrofuran (THF) in a ratio of 60:40 by weight, in an amount of 10% by weight.

After the preparation of both the ethyl cellulose solution (101) and the polycaprolactone solution (102), the solutions are then mixed at a ratio of 50:50 by weight (103).

In the production method of the artificial blood vessel (100) according to present invention; after mixing of the ethyl cellulose solution with polycaprolactone solution (103) a solution of collagen, preferably dissolved in acetic acid, is added to the solution comprising ethyl cellulose and polycaprolactone, such that the mixture comprise 0.1% of collagen by weight (104). The resulting final mixture is mixed, preferably stirred on a magnetic stirrer, preferably for 10 minutes, to obtain a homogeneous solution (105).

In the artificial blood vessel production method of the invention (100), after obtaining a homogenous solution (105), the obtained mixture is transferred to an injector and loaded to the pump section of an electrospinning machine, which leads to progression of a predetermined amount of polymer at a predetermined time interval. The flow rate of the mixture loaded in the electrospinning machine preferably has a value of 1.75 ml/h The voltage of the electricity that is then applied to provide the production of nanofibers is preferably about 36 kV. In the artificial blood vessel production method according to the invention (100), hollow nano-composite scaffolds are obtained in a cylindrical structure by collecting the nanofibers obtained by electrospinning (106) for 3 to 5 hours and collecting the electrospun fibers on a movable collector having a cylindrical structure. In said method (100), the electrospinning process (106) is preferably carried out for 4 hours. In the artificial blood vessel manufacturing method of the invention (100), in a preferred embodiment the diameter of the cylindrical structured collector used in the electrospinning process is 0.5 cm.

In the artificial blood vessel manufacturing method (100) according to the present invention, the obtained nanocomposite scaffold is dried in a 23 to 50° C. oven for 3 to 8 hours to obtain an artificial blood vessel (108). In a preferred embodiment of the invention, the nano composite scaffold is dried for 4 hours at 35° C. in an oven. The obtained artificial blood vessel can be used by cutting the blood vessel at a certain length.

Experimental studies carried out in order to achieve the object of the method (100) of the present invention aim to combine the different properties of polycaprolactone (PCL), ethyl cellulose (EC) and collagen in a single final product by means of electrospinning technique and, it is aimed to have as fine fiber dimensions as possible so that this final product should not be prone to clotting and would support cell attachment at the maximum level with help of the maximized surface area.

In the method according to the invention, firstly a solvent stock solution is prepared by mixing dimethylacetamide (DMA) and tetrahydrofuran (THF) in a weight ratio of (60:40). Afterwards, polycaprolactone (PCL) was dissolved in this stock solution in a 10% weight ratio.

In experimental studies to achieve the purpose of method of the invention (100), six different samples were prepared at different concentrations to compare the biocompatibility of the subject blood vessel with in vivo tests.

For this purpose, three separate solutions were prepared at different concentrations, namely comprising 0.5%, 0.75% and 1.0% of ethyl cellulose (EC) by weight in the stock solution. Afterwards, into every solution comprising ethyl cellulose (EC), the solution comprising 10% by weight polycaprolactone has been added such that in the final mixture the solutions have a ratio of 50:50 by weight. Then each of the 3 separate samples obtained in this way were divided into two groups. Then one group of each sample was taken and an addition of collagen dissolved in acetic acid was added such that there will be 0.1% collagen in the final mixture. The final mixture was stirred for 10 minutes to obtain a homogeneous solution in the magnetic stirrer.

The weight ratios of 6 different solutions obtained in this way are given in Table 1.

TABLE 1

The weight content of 6 different samples prepared are shown below.

|  | Group I | | Group II | | |
| --- | --- | --- | --- | --- | --- |
|  | PCL | EC | PCL | EC | Collagen |
| Sample I | 10% | 0.5% |  |  |  |
| Sample II | 10% | 0.75% |  |  |  |
| Sample III | 10% | 1% |  |  |  |
| Sample IV |  |  | 10% | 0.5% | 0.1% |
| Sample V |  |  | 10% | 0.75% | 0.1% |
| Sample VI |  |  | 10% | 1% | 0.1% |

Each sample was then loaded into the precision digital pump of the electrospinning apparatus via a 10 ml plastic syringe and delivered into the electric field at a flow rate of 1.75 ml/hr. The voltage of the electric field is set at 36.5 kV. In the mean time, with these parameters the nanofiber structure scaffold starts to collect on the collector and the process of electrospinning was continued for 4 hours. After the end of the electrospinning process, the formed nano composite scaffold was left to stand at 35° C. for 4 hours to remove solvent residues. After the required characterization tests in vitro cytotoxicity results were measured for 24, 48, 72 hours in 6 different samples for biocompatibility assessments (FIG. 2).

In accordance with the biocompatibility results given in FIG. 2, sample VI was selected for in vivo applications. For comparative analysis, Sample III which did not comprise collagen was used for in vivo applications. For this, said solutions were subjected to electrospinning process such that the obtained nanocomposite structure scaffold would form on a stainless steel collector having 0.5 cm diameter was used to obtain morphologically similar scaffolds. As a result of the electrospinning process, Nano composite scaffolds with a length of 12 cm and a weight of 6 g and an internal diameter of 0.5 cm were obtained. The obtained structure was prepared for in-vivo testing by separating the scaffold from the collector and keeping it hollow while maintaining the cylindrical structure. The blood vessels obtained from Example I III (collagen-free) and Example VI (with collagen) that are used for in-vivo studies are implanted into the animal without use of catheters etc. Finally, pathological examinations were performed and comparative analysis photographs of tissue responses are given in FIG. 4. In the collagen-free sample, the reaction of the immune system, which is the response to the artificial blood vessel by the tissue, is observed. In the case of collagen-containing sample, it is observed that the artificial blood vessel demonstrates a high biocompatibility in the animal, so it does not lead to tissue proliferation, is not invaded by defense cells and a minimum of inflammation, which is the tissue response to foreign material is observed and formation of a protective pseudo-capsule adventitia around the artificial blood vessel of the living body was seen. This is the basis for endothelialization.

By the method of the invention (100), nanofibers are produced with synergies obtained by use of natural and synthetic polymers at specific ratios, and these nanofibers are overlaid to form a nanocomposite structure scaffold with the nano composite structure scaffold, biomimetic blood vessels which have small diameter compared known artificial blood vessels are produced and these mimic natural blood vessels morphologically and physiologically with high biocompatibility.

Around this basic concepts, it is possible to develop a wide variety of applications for the invention subject matter "Biomimetic Artificial Blood Vessel and a Production Method (100) thereof" and the invention is not limited to the examples described herein, but is essentially as specified in the claims.

The invention claimed is:

1. A method for producing an artificial blood vessel, the method comprising:
    preparing an ethyl cellulose solution by dissolving a natural ethyl cellulose polymer in at least one organic solvent;
    preparing a polycaprolactone solution by dissolving a synthetic polycaprolactone polymer in another at least one organic solvent;
    mixing the ethyl cellulose solution with the polycaprolactone solution;
    adding a collagen into the mixture of the ethyl cellulose solution and the polycaprolactone solution, the collagen being dissolved in a further at least one organic solvent;
    stirring the mixture of the ethyl cellulose solution and the polycaprolactone solution and the added collagen into a homogenous solution;
    subjecting the homogenous solution to an electrospinning process for a period of time in an electrospinning machine, the electrospinning machine having at least one needle and a movable cylindrical collector;
    adjusting parameters of a voltage and a distance between the needle and the movable cylindrical collector and a flow rate of the homogenous solution to the electrospinning machine so as to effect to nanofiber diameter and morphology;
    obtaining a hollow nano-composite structure scaffold by subjecting the homogenous solution to electrospinning;
    collecting nano-fibers from the hollow nano-composite structure scaffold formed by movement of the homogenous solution with static electricity applied thereto so that the nanofibers are collected on the movable cylindrical collector; and
    drying the collected nanofibers from the movable cylindrical collector so as to form the artificial blood vessel.

2. The method of claim 1, wherein the ethyl cellulose polymer is dissolved in the one at least one organic solvent such that the ethyl cellulose polymer is 1% by weight of the ethyl cellulose solution.

3. The method of claim 1, wherein the ethyl cellulose solution has dimethylacetamide and tetrahydrofuran in a weight ratio of 60:40.

4. The method of claim 1, wherein the polycaprolactone solution has 10% by weight of the polycaprolactone polymer therein.

5. The method of claim 1, wherein the another at least one organic solvent has dimethylacetamide and hydrofuran in a weight ratio of 60:40.

6. The method of claim 1, wherein the ethyl cellulose solution and the polycaprolactone solution are mixed in a weight ration of 50:50.

7. The method of claim 1, wherein the further at least one organic solvent is acetic acid.

8. The method of claim 1, wherein the collagen is added to the mixture of ethyl cellulose solution and polycaprolactone solution such that collagen is 0.1% by weight of the mixture.

9. The method of claim 1, wherein the step of stirring comprising:
   magnetically stirring the mixture of the ethyl solution and the polycaprolactone solution for ten minutes.

10. The method of claim 1, further comprising:
    transferring the mixture of the ethyl cellulose solution and the polycaprolactone solution and the collagen to an injector; and
    loading the transferred mixture to a pump section of the electrospinning machine.

11. The method of claim 1, wherein the flow rate is 1.75 ml/hr.

12. The method of claim 1, wherein the voltage is 36 KV.

13. The method of claim 1, wherein the electrospinning is for a period of between three hours and five hours.

14. The method of claim 13, wherein the electrospinning is for a period of four hours.

15. The method of claim 1, wherein the movable cylindrical collector has a diameter of 0.5 centimeters.

16. The method of claim 1, wherein the drying is in an oven and at a temperature of between 23° C. and 50° C.

17. The method of claim 6, wherein the drying is at the temperature of 35° C.

18. The method of claim 16, wherein the drying is for a time period of between three hours and eight hours.

19. The method of claim 18, wherein the drying is for the time period of four hours.

20. An artificial blood vessel obtained by the method of claim 1.

* * * * *